(12) United States Patent
Chapman et al.

(10) Patent No.: US 8,183,251 B2
(45) Date of Patent: May 22, 2012

(54) HYDANTOIN COMPOUNDS AND PHARMACEUTICAL COMPOSITIONS THEREOF

(75) Inventors: David Chapman, Lund (SE); Balint Gabos, Lund (SE); Magnus Munck af Rosenschöld, Lund (SE)

(73) Assignee: AstraZeneca AB, Södertälje (SE)

( * ) Notice: Subject to any disclaimer, the term of this patent is extended or adjusted under 35 U.S.C. 154(b) by 1046 days.

(21) Appl. No.: 11/946,517

(22) Filed: Nov. 28, 2007

(65) Prior Publication Data

US 2008/0221139 A1 Sep. 11, 2008

Related U.S. Application Data

(60) Provisional application No. 60/867,606, filed on Nov. 29, 2006.

(51) Int. Cl.
C07D 403/12 (2006.01)
C07D 239/34 (2006.01)
A61K 31/506 (2006.01)
(52) U.S. Cl. ........................ 514/269; 544/298
(58) Field of Classification Search .................. 544/298; 514/269
See application file for complete search history.

(56) References Cited

U.S. PATENT DOCUMENTS

| | | | |
|---|---|---|---|
| 2,327,890 A | 8/1943 | Henze | |
| 2,745,875 A | 5/1956 | Ehrhart et al. | |
| 3,452,040 A | 6/1969 | Langis | |
| 3,529,019 A | 9/1970 | Suh et al. | |
| 3,849,574 A | 11/1974 | Suh et al. | |
| 4,241,073 A | 12/1980 | Jamieson et al. | |
| 4,315,031 A | 2/1982 | Vincent et al. | |
| 4,983,771 A | 1/1991 | Bryker et al. | |
| 5,068,187 A | 11/1991 | Takeichi et al. | |
| 5,246,943 A | 9/1993 | Blankley et al. | |
| 5,308,853 A | 5/1994 | Hodges et al. | |
| 5,521,187 A | 5/1996 | Freyne et al. | |
| 5,804,593 A | 9/1998 | Warpehoski et al. | |
| 5,919,790 A | 7/1999 | Allen et al. | |
| 5,955,435 A | 9/1999 | Baxter et al. | |
| 6,046,214 A | 4/2000 | Kristiansen et al. | |
| 6,048,841 A | 4/2000 | Baxter et al. | |
| 6,114,361 A | 9/2000 | Robinson et al. | |
| 6,159,995 A | 12/2000 | Thorwart et al. | |
| 6,166,041 A | 12/2000 | Cavalla et al. | |
| 6,218,418 B1 | 4/2001 | Pevarello et al. | |
| 6,268,379 B1 | 7/2001 | Xue et al. | |
| 6,277,987 B1 | 8/2001 | Kukkola et al. | |
| 6,291,685 B1 | 9/2001 | Junghans et al. | |
| 6,329,418 B1 | 12/2001 | Cheng et al. | |
| 6,339,101 B1 | 1/2002 | Ross et al. | |
| 6,340,691 B1 | 1/2002 | Levin et al. | |
| 6,429,213 B1 | 8/2002 | Xue et al. | |
| 6,890,915 B2 | 5/2005 | Sheppeck et al. | |
| 6,906,053 B2 | 6/2005 | Sheppeck et al. | |
| 7,078,424 B2 | 7/2006 | Hamilton et al. | |
| 7,132,434 B2 | 11/2006 | Eriksson et al. | |
| 7,354,940 B2 | 4/2008 | Henriksson et al. | |
| 7,368,465 B2 | 5/2008 | Eriksson et al. | |
| 7,427,631 B2 | 9/2008 | Eriksson et al. | |
| 7,625,934 B2 | 12/2009 | Eriksson et al. | |
| 7,648,992 B2 | 1/2010 | Gabos et al. | |
| 7,655,664 B2 | 2/2010 | Gabos et al. | |
| 7,662,845 B2 | 2/2010 | Henriksson et al. | |
| 7,666,892 B2 * | 2/2010 | Eriksson et al. ............... 514/389 |
| 7,700,604 B2 | 4/2010 | Gabos et al. | |
| 7,754,750 B2 | 7/2010 | Eriksson et al. | |
| 7,772,403 B2 | 8/2010 | Cornwall et al. | |
| 2002/0006920 A1 | 1/2002 | Robinson et al. | |
| 2002/0028835 A1 | 3/2002 | Hu et al. | |
| 2002/0065219 A1 | 5/2002 | Naidu et al. | |
| 2002/0091107 A1 | 7/2002 | Madar et al. | |
| 2003/0130273 A1 | 7/2003 | Sheppeck et al. | |
| 2004/0044215 A1 | 3/2004 | Alcade et al. | |
| 2004/0106659 A1 | 6/2004 | Af Rosenschold | |
| 2004/0110809 A1 | 6/2004 | Lepisto et al. | |
| 2004/0116486 A1 | 6/2004 | Lepisto et al. | |
| 2004/0127528 A1 | 7/2004 | Eriksson et al. | |

(Continued)

FOREIGN PATENT DOCUMENTS

EP 0175312 3/1986

(Continued)

OTHER PUBLICATIONS

Aharony et al. "Pharmacological Characterization of a New Class of Nonpeptide Neurokinin A Antagonists that Demonstrate Species Selectivity." J. Pharmacol. Exp. Ther. 274:3 (1995), pp. 1216-1221.

Aigner et al., "Growth Plate Cartilage as Developmental Model in Osteoarthritis Research-Potentials and Limitations", *Current Drug Targets* 8(2):377-385 (2007).

Aimoto et al. "Synthesis of Carriers of Differing Strokes Radius with Activated Acyl Groups for Use as Reagents in Labeling Membrane Proteins." Journal of Biological Chemistry, vol. 256(10), pp. 5134-5143, 1981.

(Continued)

*Primary Examiner* — Deepak Rao
(74) *Attorney, Agent, or Firm* — Fish & Richardson P.C.

(57) ABSTRACT

The invention provides compounds of formula (I):

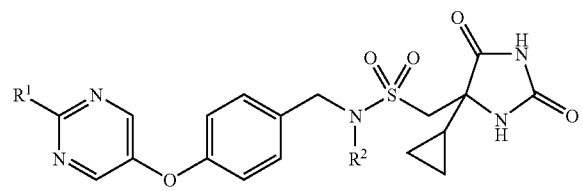

wherein $R^1$ and $R^2$ are as defined in the specification; processes for their preparation; pharmaceutical compositions containing them; a process for preparing the pharmaceutical compositions; and their use in therapy. The compounds are useful as MMP inhibitors.

11 Claims, No Drawings

U.S. PATENT DOCUMENTS

| | | |
|---|---|---|
| 2004/0138276 A1 | 7/2004 | Eriksson et al. |
| 2004/0147573 A1 | 7/2004 | Eriksson et al. |
| 2004/0152697 A1 | 8/2004 | Chan et al. |
| 2004/0209874 A1 | 10/2004 | Sheppeck et al. |
| 2004/0266832 A1 | 12/2004 | Li et al. |
| 2005/0019994 A1 | 1/2005 | Chang |
| 2005/0026990 A1 | 2/2005 | Eriksson et al. |
| 2005/0171096 A1 | 8/2005 | Sheppeck et al. |
| 2005/0245586 A1 | 11/2005 | Henriksson et al. |
| 2005/0256176 A1 | 11/2005 | Burrows et al. |
| 2006/0019994 A1 | 1/2006 | Burrows et al. |
| 2006/0063818 A1 | 3/2006 | Burrows et al. |
| 2006/0276524 A1 | 12/2006 | Henriksson et al. |
| 2008/0004317 A1 | 1/2008 | Gabos et al. |
| 2008/0032997 A1 | 2/2008 | Gabos et al. |
| 2008/0064710 A1 | 3/2008 | Gabos et al. |
| 2008/0171882 A1 | 7/2008 | Eriksson et al. |
| 2008/0221139 A1 | 9/2008 | Chapman et al. |
| 2008/0262045 A1 | 10/2008 | Eriksson et al. |
| 2008/0293743 A1 | 11/2008 | Gabos et al. |
| 2008/0306065 A1 | 12/2008 | Eriksson et al. |
| 2009/0054659 A1 | 2/2009 | Cornwall et al. |
| 2009/0221640 A1 | 9/2009 | Briggner et al. |
| 2010/0144771 A1 | 6/2010 | Gabos et al. |
| 2010/0256166 A1 | 10/2010 | Gabos et al. |
| 2010/0273849 A1 | 10/2010 | Eriksson et al. |
| 2011/0003853 A1 | 1/2011 | Eriksson et al. |

FOREIGN PATENT DOCUMENTS

| | | |
|---|---|---|
| EP | 0212617 | 3/1987 |
| EP | 0255390 | 2/1988 |
| EP | 0442584 | 8/1991 |
| EP | 0486280 | 5/1992 |
| EP | 0580210 | 1/1994 |
| EP | 0640594 | 3/1995 |
| EP | 0709375 | 5/1996 |
| EP | 1397137 | 11/1996 |
| EP | 0909754 | 4/1999 |
| EP | 1117616 | 7/2001 |
| EP | 1149843 | 10/2001 |
| EP | 1191024 | 3/2002 |
| EP | 1550725 | 7/2005 |
| WO | WO 92/01062 | 1/1992 |
| WO | WO 95/14025 | 5/1995 |
| WO | WO 96/21640 | 7/1996 |
| WO | WO 96/27583 | 9/1996 |
| WO | WO 98/50359 | 11/1998 |
| WO | WO 99/06361 | 2/1999 |
| WO | WO 99/24399 | 5/1999 |
| WO | WO 99/42443 | 8/1999 |
| WO | WO 99/62880 | 12/1999 |
| WO | WO 00/09103 | 2/2000 |
| WO | WO 00/12477 | 3/2000 |
| WO | WO 00/12478 | 3/2000 |
| WO | WO 00/35886 | 6/2000 |
| WO | WO 00/40577 | 7/2000 |
| WO | WO 00/44770 | 8/2000 |
| WO | WO 00/75106 | 12/2000 |
| WO | WO 01/05756 | 1/2001 |
| WO | WO 01/12189 | 2/2001 |
| WO | WO 01/22363 | 3/2001 |
| WO | WO 01/34573 | 5/2001 |
| WO | WO 02/06232 | 1/2002 |
| WO | WO 02/14262 | 2/2002 |
| WO | WO 02/14354 | 2/2002 |
| WO | WO 02/20515 | 3/2002 |
| WO | WO 02/074748 | 9/2002 |
| WO | WO 02/074749 | 9/2002 |
| WO | WO 02/074750 | 9/2002 |
| WO | WO 02/074751 | 9/2002 |
| WO | WO 02/074752 | 9/2002 |
| WO | WO 02/074767 | 9/2002 |
| WO | WO 02/096426 | 12/2002 |
| WO | WO 03/040098 | 5/2003 |
| WO | WO 03/087057 | 10/2003 |
| WO | WO 03/093260 | 11/2003 |
| WO | WO 03/094919 | 11/2003 |
| WO | WO 2004/020415 | 3/2004 |
| WO | WO 2004/024060 | 3/2004 |
| WO | WO 2004/024698 | 3/2004 |
| WO | WO 2004/024715 | 3/2004 |
| WO | WO 2004/024718 | 3/2004 |
| WO | WO 2004/024721 | 3/2004 |
| WO | WO 2004/033632 | 4/2004 |
| WO | WO 2004/108086 | 12/2004 |
| WO | WO 2006/004532 | 1/2006 |
| WO | WO 2006/004533 | 1/2006 |
| WO | WO 2006/065215 | 6/2006 |
| WO | WO 2006/065216 | 6/2006 |
| WO | WO 2006/077387 | 7/2006 |
| WO | WO 2007/106021 | 9/2007 |
| WO | WO 2007/106022 | 9/2007 |

OTHER PUBLICATIONS

Avgeropoulos et al., "New Treatment Strategies for Malignant Gliomas", *The Oncologist* 4:209-224 (1999).

Banfield et al., "Heterocyclic Derivatives of Guanidine. Part V. Reaction of Some Glycidic Esters with Guanidines", *The Journal of the Chemical Society* 511:2747-2756 (1963).

Belvisi et al., "The role of matrix metalloproteinases (MMPs) in the patho-physiology of chronic obstructive pulmonary disease (COPD): a therapeutic role for inhibitors of MMPs?", *Inflammation Research* 52:95-100 (2003).

Borchers et al., "Acrolein-Induced MUC5ac Expression in Rat Airways", *The American Physiological Society* 274:L573-L581 (1998).

Borkakoti, "Matrix metalloprotease inhibitors: design from structure", *Biochemical Society Transactions* 32:17-20 (2004).

Bright et al. "Monoclonal Antibodies as Surrogate Receptors in High Throughput Screen for Compounds that Enhance Insulin Sensitivity." Life Sciences. 61:23 (1997), pp. 2305-2315.

Bruce et al., "The effect of marimastat, a metalloprotease inhibitor, on allergen-induced asthmatic hyper-activity", *Toxicol. & Appl. Pharmacol.* 205:126-132 (2005).

Carmeliet, "Proteinases in Cardiovascular Aneurysms and Rupture: Targets for Therapy?", *The Journal of Clinical Investigation* 105(11):1519-1520 (2000).

Catterall et al., "Drugs in development: bisphosphonates and metalloproteinase inhibitors", *Arthritis Res Ther* 5:12-24 (2003).

Chambers et al., "Changing Views of the Role of Matrix Metalloproteinases in Metastasis", *J Natl Cancer Inst* 89:1260-1270 (1997).

Chemical Abstracts, vol. 65, 1966, ABSTRACT No. 13684 h, M. Lora-Tamayo et al.: "Potential anticancer agents. I. Glutamine sulfonate analogs", & Anales Real Soc. Espan. Fis. Quim (Madrid), Ser. B. 62(2), 173-86.

Chodosh et al., "Comparative trials of doxycycline versus amoxicillin, cephalexin and enoxacin in bacterial infections in chronic bronchitis and asthma", *Scand. J. Infect. Dis. Suppl.* 53:22-8 (1988).

Comber et al., "5,5-Disubstituted Hydantoins: Syntheses and Anti-HIV Activity", *J Med. Chem.* 35:3567-3572 (1992).

COPD; http://www.lungsonline.com/copd.html, downloaded Aug. 22, 2008.

Croce, P. et al. "Stereoselective aldol addition of a chiral glycine enloate synthon to heteroaromatic aldehydes." Heterocycles, 52:3 (2000) pp. 1337-1344.

Dahan et al., "Expression of Matrix Metalloproteinases in Healthy and Diseased Human Gingiva", *Journal of Clinical Periodontology* 28:128-136 (2001).

Demedts et al., "Elevated MMP-12 protein levels in induced sputum from patients with COPD", *Thorax* 61:196-201 (2006).

Doherty et al., "Therapeutic Developments in Matrix Metalloproteinase Inhibition", *Expert Opinion Ther. Patents* 12(5):665-707 (2002).

Dormán et al., "MMP Inhibitors in Cardiac Diseases: An Update", *Recent Patents on Cardiovascular Drug Discovery* 2:000-000 (2007).

Dorwald, F.Z., "Side Reactions in Organic Synthesis: A Guide to Successful Synthesis Design", 2005, Wiley-VCH Verlag GmbH & Co. KGaA, Weinheim.

Doxycycline hyclate; http://en.wikipedia.org/wiki/Doxycycline_hyclate, downloaded Aug. 22, 2008.
Elliot et al., "The Clinical Potential of Matrix Metalloproteinase Inhibitors in the Rheumatic Disorders", *Drugs & Aging* 18(2):87-99 (2001).
Fujita et al., "The pathogenesis of COPD: Lessons Learned from in vivo Animal Models", *Med. Sci Monit.* 13(2):RA19-24 (2007).
Gramatica et al., STN International, HCAPLUS Database, Columbus, OH, Accession No. 2002:356947, Reg. No. 36734-19-7.
Hautamaki et al., "Requirement for Macrophage Elastase for Cigarette Smoke-Induced Emphysema in Mice", *Science* 277:2002-2004 (2002).
Hirrlinger et al., "Purification and properties of an amidase from Rhodococcus erythropolis MP50 which enantioselectively hydrolyzes 2-arylpropionamides", *J. Bacteriology* 178(12):3501-3507 (1996).
Johnson et al., "Divergent effects of matrix metalloproteinases 3, 7, 9, and 12 on atherosclerotic plaque stability in mouse brachiocephalic arteries", *PNAS* 102(43):15575-15580 (2005).
Kelly et al., "Role of matrix metalloproteinase in asthma", *Current Opinion in Pulmonary Medicine* 9(1):28-33 (2003).
Knabe, J. "Razemate und enantiomere basisch substituierter 5-phenylhydantoine." Pharmazie. 52:12 (1997) pp. 912-919.
Lindy et al., "Matrix Metalloproteinase 13 (Collagenase 3) in Human Rheumatoid Synovium Arthritis Rheumatism," *Arthritis and Rheumatism* 40(8):1391-1399 (1997).
Lora-Tamayo et al. "Anticancerousos Potenciales." An. Quim. 64:6 (1968), pp. 591-606.
MacFadyen, "Can Matrix Metalloproteinase Inhibitors Provide a Realistic Therapy in Cardiovascular Medicine", *Current Opinion in Pharmacology* 7:171-178 (2007).
Mandal, Malay et al., "*Clinical Implications of Matrix Metalloproteinases*", *Molecular and Cellular Biochemistry*, 252:305-329, (2003).
Michaelides et al., "Recent Advances in Matrix Metalloproteinase Inhibitors Research", *Current Pharmaceutical Design* 5:787-819 (1999).
Miyake, Toshiaki et al. "Studies on Glycosylation of erythro-Beta-Hydroxy-L-histidine. A Key Step of Blemycin Total Synthesis." Bull. Chem. Soc. Jpn. 59 (1986), pp. 1387-1395.
Mock et al., "Principles of Hydroxamate Inhibition of Metalloproteases: Carboxypeptidase A", *Biochemistry* 39:13945-13952 (2000).
Morris et al., PubMed Abstract, "Sequential steps in hematogenous metastasis of cancer cells studied by in vivo videomicroscopy", *Invasion Metastasis* 17:281-296 (1997).
Murphy et al., "Reappraising metalloproteinases in rheumatoid arthritis and osteoarthritis: destruction or repair?", *Nature Clinical Practice Rheumatology* 4:128-135 (2008).
Nakajima, Riichiro et al. "The utility of 4-(2-thienyl)pyridines as a derivatization reagent for hplc and ce." Analytical Sciences. 7, Supplement 1991, pp. 177-180.
Nicolet, Ben. "Interpretation of the Dyhydration of Acetylglutamic acid by Means of Glutamylthiohydantoin Derivatives." Journal of the American Chemical Society, 1930, pp. 1192-1195.
Owa, Takashi et al. "Man-Designed Bleomycins: Significance of the binding Sites as Enzyme Models and of the Stereochemistry of the Linker Moiety." Tetrahedron. 48:7 (1992) pp. 1193-1208.
Peng, Sean X. "Separation and identification of methods for metalloproteinase inhibitors." Journal of Chromatography B. 764 (2001), pp. 59-80.
Pyo et al., "Targeted gene disruption of matrix metalloproteinase-9 (gelatinase B) suppresses development of experimental abdominal aortic aneurysms", *J Clinical Investigation* 105:1641-1649 (2000).
Rasmussen et al., "Matrix Metalloproteinase Inhibition as a Novel Anticancer Strategy: A Review with Special Focus on Batimastat and Marimastat", *Pharmacol. Ther.* 75:69-75 (1997).
Reisner, "Some α-amino acids containing a sulfonamide group", *J Am. Chem. Soc.* 78:5102-5104 (1956). CAS abstract and search structure only.
Rifkin et al, "Blocking Periodontal Disease Progression by Inhibiting Tissue-Destructive Enzymes: A Potential Therapeutic Role for Tetracyclines and Their Chemically-Modified Analogs", Periodontol 1993 Aug. 64 (8 Suppl), pp. 819-827.
Rouis et al., "Adenovirus-mediated overexpression of tissue inhibitor of metalloproteinase-1 reduces atherosclerotic lesions in apolipoprotein E-deficient mice", *Circulation* 100:533-540 (1999).
Saito, Sei-ichi et al. "A new synthesis of deglyco-bleomycine A2 aiming at the total synthesis of bleomycin." Tetrahedron Letters. 23(5) (1982), pp. 529-532.
Simone, "Oncology: Introduction", Cecil Textbook of Medicine, 20th Edition, vol. 1, pp. 1004-1010 (1996).
Smith, Michael B., Organic Synthesis Second Edition, 3.9.A Oxidation of sulfur compounds, McGraw-Hill 2002, ISBN-0-07-048242-X, p. 280.
STN International, file CAPLUS, accession No. 1978:424767, Raulais, Daniel J.P., "Synthesis and characterization of phenylthiohydantoin derivatives of amino-acids protected in their sid-chain functions, and their application for monitoring olid-phase peptide synthesis," & Journal of Chemical Research, Synopses (1978), p. 11.
STN International, file CAPLUS, accession No. 1994:299315, Document No. 120:299315, Sakamoto, Shuichi et al., "Preparation of pyridylserine derivatives as psychotropics," WO, A1, 9320053, 19931014, See CAS RN 154696-31-8, 154697-48-0.
STN International, file CAPLUS, accession No. 1997:644516, Batty, Craig et al. "Synthesis and exchange reaction of 5-alkyl-2oxo-6-thioxo-1,2,3,6-hexahydropyrimidine-4-carboxylic acids" & Journal of Heterocyclic Chemistry (1997), 34:3, 1355-1367.
STN International, file CAPLUS, accession No. 2002:640897, Gooding, Owen W. et al. "Use of Statistical Design of Experiments in the Optimization of Amide Synthesis Utilizing Polystryene-Supported N-Hydroxybenzotriazole Resin" & Journal of Combinatorial Chemistry (2002), 4(6), 576-583.
STN International, File CAPLUS, CAPLUS accession No. 1968:506154, Doc. No. 69:106154, Lora-Tamayo, J. et al.: "Potential anticancer agents, VI. Sulfonic analogs of aspartic acid", & An. Quim. (1968), 64(6), 591-606.
STN International, File CAPLUS, CAPLUS accession No. 1974:463633, Doc. No. 81:63633, Blaha, Ludvik et al.: "5-Methyl-5-phenoxymethyl-hydantoins", & CS 151744, B, 19731119.
STN International, File CAPLUS, CAPLUS accession No. 1988:631020, Doc. No. 109:231020, Mitsui Toatsu Chemicals, Inc.: "Process for the preparation of 5-benzylhydantoins as intermediates for aromatic amino acids": & JP, A2, 63079879, 19880409.
STN International, File CAPLUS, CAPLUS accession No. 1989:173366, Doc. No. 110:173366, Oh, Chang Hyun et al., "Synthesis of new hydantoin-3-acetic acid derivatives", & Bull. Korean Chem. Soc. (1988), 9(4), 231-5.
STN International, File CAPLUS, CAPLUS accession No. 1990:138955, Doc. No. 112:138955, Crooks, Peter A. et al.: "Synthesis of 5-benzoyl-5-phenyl-and-5-(Phenylhydroxymethyl)-5-phenylhydantoins as potential anticonvulsants"; & J. Heterocycl. Chem. (1989), 26(4), 1113-17.
Visse et al., "Matrix Metalloproteinases and Tissue Inhibitors of Metalloproteinases", *Circ Res.* 92:827-839 (2003).
Wernicke, Dirk et al., "*Cloning of Collagenase 3 from the Synovial Membrane and Its Expression in Rheumatoid Arthritis and Osteoarthritis*", *The Journal of Rheumatology.* 23:590-595, (1996).
Whittaker, Mark et al., "*Design and Therapeutic Application of Matrix Metalloproteinase Inhibitors*", *Chemical Reviews*, 99:2735-2776, (1999).
Wikipedia, Matrix metalloproteinase, updated Mar. 09, 2009, <http://en.wikipedia.org/wiki/Matrix_metalloproteinase>, downloaded Mar. 11, 2009.
Wikipedia, Minocycline, updated Feb. 28, 2009, http://en.wikipedia.org/wiki/Minocycline, downloaded Mar. 11, 2009.
Wingerchuk, Dean M. et al., "Multiple Sclerosis: Current Pathophysiological Concepts", Biology of Disease, Lab Invest 2001, vol. 81, pp. 263-281.
USPTO Restriction Requirement in U.S. Appl. No. 10/471,810, filed Jun. 23, 2006, 11 pages.
Fish & Richardson P.C., Response to Restriction Requirement of Jun. 23, 2006 in U.S. Appl. No. 10/471,810, filed Jul. 24, 2006, 5 pages.

USPTO Non-Final Office Action in U.S. Appl. No. 10/471,810, mailed Jan. 12, 2007, 15 pages.
Fish & Richardson P.C., Amendment in Reply to Action of Jan. 12, 2007 in U.S. Appl. No. 10/471,810, filed Apr. 12, 2007, 14 pages.
Fish & Richardson P.C., Supplemental Amendment in U.S. Appl. No. 10/471,810, filed Jun. 8, 2007, 11 pages.
USPTO Notice of Allowance in U.S. Appl. No. 10/471,810, mailed Jun. 21, 2007, 13 pages.
Fish & Richardson P.C., RCE and Supplemental Amendment in Reply to Notice of Allowance of Jun. 21, 2007 in U.S. Appl. No. 10/471,810, filed Sep. 21, 2007, 16 pages.
USPTO Notice of Allowance in U.S. Appl. No. 10/471,810, mailed Dec. 7, 2007, 6 pages.
Fish & Richardson P.C., Response to Notice of Allowance of Dec. 7, 2007 in U.S. Appl. No. 10/471,810, filed Mar. 6, 2007, 2 pages.
USPTO Restriction Requirement in U.S. Appl. No. 12/114,901, filed Dec. 1, 2008, 9 pages.
Fish & Richardson P.C., Response to Restriction Requirement of Dec. 1, 2008 in U.S. Appl. No. 12/114,901, filed Apr. 1, 2009, 12 pages.
USPTO Notice of Allowance in U.S. Appl. No. 12/114,901, filed Jun. 24, 2009, 10 pages.
Fish & Richardson P.C., RCE and IDS in Reply to Notice of Allowance of Jun. 24, 2009 in U.S. Appl. No. 12/114,901, filed Sep. 24, 2009, 14 pages.
USPTO Notice of Allowance in U.S. Appl. No. 12/114,901, mailed Oct. 6, 2009, 17 pages.
Fish & Richardson P.C., Response to Notice of Allowance of Oct. 6, 2009 in U.S. Appl. No. 12/114,901, filed Jan. 6, 2010, 2 pages.
USPTO Non-Final Office Action in U.S. Appl. No. 12/693,852, mailed Nov. 18, 2010, 18 pages.
USPTO Non-Final Office Action in U.S. Appl. No. 12/830,763, mailed Nov. 18, 2010, 20 pages.
USPTO Non-Final Office Action in U.S. Appl. No. 12/629,630, mailed Aug. 27, 2010, 27 pages.
Fish & Richardson P.C., Amendment in Reply to Action of Aug. 27, 2010 in U.S. Appl. No. 12/629,630, filed Feb. 25, 2011, 6 pages.
USPTO Notice of Allowance in U.S. Appl. No. 12/629,630, mailed Mar. 24, 2011, 15 pages.

* cited by examiner

HYDANTOIN COMPOUNDS AND PHARMACEUTICAL COMPOSITIONS THEREOF

CROSS REFERENCE TO RELATED APPLICATIONS

This application claims the benefit of U.S. Provisional Application No. 60/867,606, filed on Nov. 29, 2006, which is incorporated herein by reference in its entirety.

FIELD OF THE INVENTION

The present invention relates to novel hydantoin derivatives, processes for their preparation, pharmaceutical compositions containing them and their use in therapy.

BACKGROUND OF THE INVENTION

Metalloproteinases are a superfamily of proteinases (enzymes) whose numbers in recent years have increased dramatically. Based on structural and functional considerations these enzymes have been classified into families and subfamilies as described in N. M. Hooper (1994) FEBS Letters 354: 1-6. Examples of metalloproteinases include the matrix metalloproteinases (MMPs) such as the collagenases (MMP1, MMP8, MMP13), the gelatinases (MMP2, MMP9), the stromelysins (MMP3, MMP10, MMP11), matrilysin (MMP7), metalloelastase (MMP12), enamelysin (MMP19), the MT-MMPs (MMP14, MMP15, MMP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteinases such as aggrecanase, the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen, proteoglycan and fibronectin. Metalloproteinases are also believed to be important in the processing, or secretion, of biological important cell mediators, such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem. J. 321:265-279).

Metalloproteinases have been associated with many diseases or conditions. Inhibition of the activity of one or more metalloproteinases may well be of benefit in these diseases or conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; extracellular matrix remodelling observed in cardiovascular diseases such as restenosis and atherosclerosis; asthma; rhinitis; and chronic obstructive pulmonary diseases (COPD).

MMP12, also known as macrophage elastase or metalloelastase, was initially cloned in the mouse by Shapiro et al [1992, Journal of Biological Chemistry 267: 4664] and in man by the same group in 1995. MMP12 is preferentially expressed in activated macrophages, and has been shown to be secreted from alveolar macrophages from smokers [Shapiro et al, 1993, Journal of Biological Chemistry, 268: 23824] as well as in foam cells in atherosclerotic lesions [Matsumoto et al, 1998, Am. J. Pathol. 153: 109]. A mouse model of COPD is based on challenge of mice with cigarette smoke for six months, two cigarettes a day six days a week. Wild-type mice developed pulmonary emphysema after this treatment. When MMP12 knock-out mice were tested in this model they developed no significant emphysema, strongly indicating that MMP12 is a key enzyme in the COPD pathogenesis. The role of MMPs such as MMP12 in COPD (emphysema and bronchitis) is discussed in Anderson and Shinagawa, 1999, Current Opinion in Anti-inflammatory and Immunomodulatory Investigational Drugs 1 (1): 29-38. It was recently discovered that smoking increases macrophage infiltration and macrophage-derived MMP-12 expression in human carotid artery plaques Kangavari [Matetzky S, Fishbein M C et al., Circulation 102:(18), 36-39 Suppl. S, Oct. 31, 2000].

Clinical studies with matrix metalloproteinase inhibitors have frequently revealed adverse side effects referred to as the musculoskeletal syndrome. Such side effects have prevented the further development of certain matrix metalloproteinase inhibitor drug candidates. Several hypotheses based upon a lack of selectivity for these drug candidates among the different matrix metalloproteinases have been advanced to explain the musculoskeletal syndrome (see, for example, J. Thomas Peterson, Cardiovascular Research, 69 (2006): 677-687). In order to minimise any possible adverse musculoskeletal side effects, there is a clear rational to develop selective MMP-12 inhibitors for the treatment of MMP-12 mediated human disease.

A number of metalloproteinase inhibitors are known (see, for example, the reviews of MMP inhibitors by Beckett R. P. and Whittaker M., 1998, Exp. Opin. Ther. Patents, 8 (3):259-282; and by Whittaker M. et al, 1999, Chemical Reviews 99 (9):2735-2776).

WO 02/074751 discloses hydantoin derivatives of formula

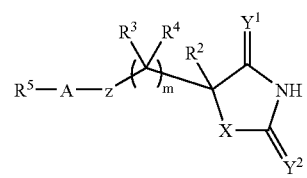

that are useful as MMP inhibitors.

We now disclose a further group of hydantoin derivatives that are inhibitors of metalloproteinases and are of particular interest as potent and selective inhibitors of MMP12. The compounds of the present invention have beneficial potency, selectivity and/or pharmacokinetic properties.

DISCLOSURE OF THE INVENTION

In accordance with the present invention, there are provided compounds of formula (I)

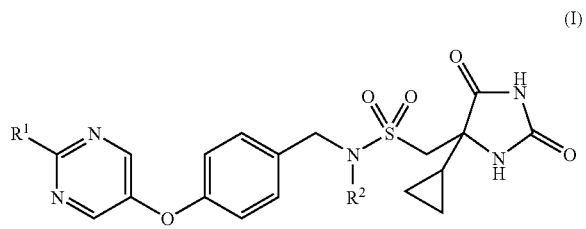

(I)

wherein $R^1$ represents H, $CH_3$, $CH_3CH_2$, $CF_3$ or cyclopropyl; and $R^2$ represents H or $CH_3$;

and pharmaceutically acceptable salts thereof.

In one embodiment, $R^2$ represents $CH_3$.

In one embodiment, $R^1$ represents cyclopropyl or $CF_3$.

In one embodiment, $R^1$ represents cyclopropyl and $R^2$ represents $CH_3$.

In one embodiment, $R^1$ represents $CF_3$ and $R^2$ represents $CH_3$.

Examples of compounds of the invention include:

1-[(4S)-4-cyclopropyl-2,5-dioxoimidazolidin-4-yl]-N-methyl-N-{[4-(pyrimidin-5-yloxy)phenyl]methyl}methanesulfonamide;

1-[(4S)-4-cyclopropyl-2,5-dioxoimidazolidin-4-yl]-N-({-4-[(2-cyclopropylpyrimidin-5-yl)oxy]phenyl}methyl)-N-methylmethanesulfonamide;

1-[(4S)-4-cyclopropyl-2,5-dioxoimidazolidin-4-yl]-N-methyl-N-({4-[(2-methylpyrimidin-5-yl)oxy]phenyl}methyl)methanesulfonamide;

1-[(4S)-4-cyclopropyl-2,5-dioxoimidazolidin-4-yl]-N-methyl-N-[(4-{[2-(trifluoromethyl)pyrimidin-5-yl]oxy}phenyl)methyl]methanesulfonamide;

1-[(4S)-4-cyclopropyl-2,5-dioxoimidazolidin-4-yl]-N-({4-[(2-ethylpyrimidin-5-yl)oxy]phenyl}methyl)-N-methylmethanesulfonamide;

1-[(4S)-4-cyclopropyl-2,5-dioxoimidazolidin-4-yl]-N-[(4-{[2-(trifluoromethyl)pyrimidin-5-yl]oxy}benzyl)]methanesulfonamide;

and pharmaceutically acceptable salts thereof.

Each exemplified compound represents a particular and independent aspect of the invention.

The compounds of formula (I) may exist in enantiomeric forms. It is to be understood that all enantiomers, diastereomers, racemates and mixtures thereof are included within the scope of the invention. The various optical isomers may be isolated by separation of a racemic mixture of the compounds using conventional techniques, for example, fractional crystallisation, or HPLC. Alternatively the optical isomers may be obtained by asymmetric synthesis, or by synthesis from optically active starting materials.

Where optically active isomers exist in the compounds of the invention, we disclose all individual optically active forms and combinations of these as individual specific embodiments of the invention, as well as their corresponding racemates.

In one embodiment, the compounds of formula (I) have (4S)-stereochemistry as shown below:

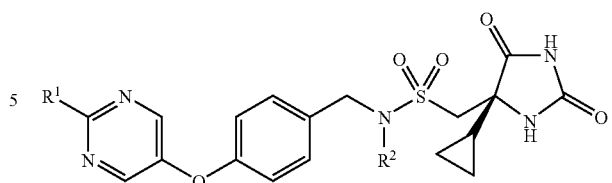

For the avoidance of doubt, the (4S)-stereoisomer may be present as a mixture with the (4R)-stereoisomer. For example, the (4S)-stereoisomer may be present in a 1:1 mixture with the (4R)-stereoisomer.

In one embodiment, the compound of formula (I) is optically pure. In the context of the present specification, the term optically pure is defined in terms of enantiomeric excess (e.e.), which is calculated from the ratio of the difference between the amounts of the respective enantiomers present and the sum of these amounts, expressed as a percentage. To illustrate, a preparation containing 95% of one enantiomer and 5% of another enantiomer has an enantiomeric excess of 90% [i.e. (95−5)/(95+5)×100]. An optically pure compound according to the present invention has an e.e. of at least 90%. In one embodiment, an optically pure compound according to the present invention has an e.e. of at least 95%. In a further embodiment, an optically pure compound according to the present invention has an e.e. of at least 98%.

Where tautomers exist for the compounds of the invention, we disclose all individual tautomeric forms and combinations of these as individual specific embodiments of the invention.

The present invention includes compounds of formula (I) in the form of salts. Suitable salts include those formed with organic or inorganic acids or organic or inorganic bases. Such salts will normally be pharmaceutically acceptable salts although non-pharmaceutically acceptable salts may be of utility in the preparation and purification of particular compounds. Such salts include acid addition salts such as hydrochloride, hydrobromide, citrate, tosylate and maleate salts and salts formed with phosphoric acid or sulphuric acid. In another aspect suitable salts are base salts such as an alkali metal salt, for example, sodium or potassium, an alkaline earth metal salt, for example, calcium or magnesium, or an organic amine salt, for example, triethylamine.

Salts of compounds of formula (I) may be formed by reacting the free base or another salt thereof with one or more equivalents of an appropriate acid or base.

The compounds of formula (I) are useful because they possess pharmacological activity in animals, particularly humans, and are thus potentially useful as pharmaceuticals. In particular, the compounds of the invention are metalloproteinase inhibitors and may thus be used in the treatment of human diseases or conditions mediated by MMP12 such as asthma, rhinitis, chronic obstructive pulmonary diseases (COPD), arthritis (such as rheumatoid arthritis and osteoarthritis), atherosclerosis and restenosis, cancer, invasion and metastasis, diseases involving tissue destruction, loosening of hip joint replacements, periodontal disease, fibrotic disease, infarction and heart disease, liver and renal fibrosis, endometriosis, diseases related to the weakening of the extracellular matrix, heart failure, aortic aneurysms, CNS related diseases such as Alzheimer's disease and multiple sclerosis (MS), and haematological disorders.

In general, the compounds of the present invention are potent and selective inhibitors of human MMP12 (hMMP12). The compounds of the present invention also show good selectivity with respect to a relative lack of inhibition of various other hMMPs such as hMMP2, hMMP8, hMMP9, hMMP14 and hMMP19.

The compounds of formula (I) and their pharmaceutically acceptable salts can be used in the treatment of diseases of the respiratory tract such as obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; adult respiratory distress syndrome (ARDS); cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

The compounds of formula (I) and their pharmaceutically acceptable salts can also be used in the treatment of diseases of bone and joints such as arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies.

The compounds of formula (I) and their pharmaceutically acceptable salts can also be used in the treatment of pain and connective tissue remodelling of musculoskeletal disorders due to injury [for example, sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis).

The compounds of formula (I) and their pharmaceutically acceptable salts can also be used in the treatment of diseases of skin such as psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, malepattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

The compounds of formula (I) and their pharmaceutically acceptable salts can also be used in the treatment of diseases of the eye such as blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial.

The compounds of formula (I) and their pharmaceutically acceptable salts can also be used in the treatment of diseases of the gastrointestinal tract such as glossitis, gingivitis, periodontitis; oesophagitis, including reflux; eosinophilic gastroenteritis, mastocytosis, Crohn's disease, colitis including ulcerative colitis, proctitis, pruritis ani; coeliac disease, irritable bowel syndrome, non-inflammatory diarrhoea, and food-related allergies which may have effects remote from the gut (for example, migraine, rhinitis or eczema).

The compounds of formula (I) and their pharmaceutically acceptable salts can also be used in the treatment of diseases of the cardiovascular system such as atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins.

The compounds of formula (I) and their pharmaceutically acceptable salts can also be used in oncology such as in the treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

In one aspect, the compounds of formula (I) and their pharmaceutically acceptable salts may be used in the treatment of adult respiratory distress syndrome (ARDS), cystic fibrosis, pulmonary emphysema, bronchitis, bronchiectasis, chronic obstructive pulmonary disease (COPD), pulmonary hypertension, asthma, rhinitis, ischemia-reperfusion injury, rheumatoid arthritis, osteoarthritis, cancer, atherosclerosis, MS, periodontal disease and gastric mucosal injury.

In another aspect, the compounds of formula (I) and their pharmaceutically acceptable salts may be used in the treatment or prophylaxis of inflammatory diseases or conditions and diseases associated with uncontrolled degradation of the extracellular matrix and remodelling.

In another aspect, the compounds of formula (I) and their pharmaceutically acceptable salts may be used in the treatment or prophylaxis of inflammatory respiratory diseases or conditions.

More particularly, the compounds of formula (I) and their pharmaceutically acceptable salts may be used in the treatment of chronic obstructive pulmonary disease (COPD), asthma and rhinitis.

Even more particularly, the compounds of formula (I) and their pharmaceutically acceptable salts may be used in the treatment of chronic obstructive pulmonary disease (COPD).

Accordingly, the present invention provides a compound of formula (I), or a pharmaceutically acceptable salt thereof, as hereinbefore defined for use in therapy.

In another aspect, the invention provides the use of a compound of formula (I), or a pharmaceutically acceptable salt thereof, as hereinbefore defined in the manufacture of a medicament for use in therapy.

In another aspect, the invention provides the use of a compound of formula (I), or a pharmaceutically acceptable salt thereof, as hereinbefore defined in the manufacture of a medicament for use in the treatment of human diseases or conditions in which inhibition of MMP12 is beneficial.

In another aspect, the invention provides the use of a compound of formula (I), or a pharmaceutically acceptable salt thereof, as hereinbefore defined in the manufacture of a medicament for use in the treatment of inflammatory disease.

In another aspect, the invention provides the use of a compound of formula (I), or a pharmaceutically acceptable salt thereof, as hereinbefore defined in the manufacture of a medicament for use in the treatment of an obstructive airways disease such as asthma or COPD.

In another aspect, the invention provides the use of a compound of formula (I), or a pharmaceutically acceptable salt thereof, as hereinbefore defined in the manufacture of a medicament for use in the treatment of rheumatoid arthritis, osteoarthritis, atherosclerosis, periodontal disease or multiple sclerosis.

In another aspect, the invention provides a compound of formula (I), or a pharmaceutically acceptable salt thereof, as hereinbefore defined for the treatment of diseases or conditions in which inhibition of MMP12 is beneficial.

In another aspect, the invention provides a compound of formula (I), or a pharmaceutically acceptable salt thereof, as hereinbefore defined for the treatment of inflammatory disease.

In another aspect, the invention provides a compound of formula (I), or a pharmaceutically acceptable salt thereof, as hereinbefore defined for the treatment of an obstructive airways disease such as asthma or COPD.

In another aspect, the invention provides a compound of formula (I), or a pharmaceutically acceptable salt thereof, as hereinbefore defined for the treatment of rheumatoid arthritis, osteoarthritis, atherosclerosis, periodontal disease or multiple sclerosis.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention further provides a method of treating, or reducing the risk of, a disease or condition in which inhibition of MMP12 is beneficial which comprises administering to a patient a therapeutically effective amount of a compound of formula (I) or a pharmaceutically acceptable salt thereof as hereinbefore defined.

The invention further provides a method of treating, or reducing the risk of, an inflammatory disease or condition which comprises administering to a patient a therapeutically effective amount of a compound of formula (I) or a pharmaceutically acceptable salt thereof as hereinbefore defined.

The invention also provides a method of treating, or reducing the risk of, an obstructive airways disease, for example, asthma or COPD, which comprises administering to a patient a therapeutically effective amount of a compound of formula (I) or a pharmaceutically acceptable salt thereof as hereinbefore defined.

For the above-mentioned therapeutic uses the dosage administered will, of course, vary with the compound employed, the mode of administration, the treatment desired and the disorder to be treated. The daily dosage of the compound of formula (I)/salt (active ingredient) may be in the range from 0.001 mg/kg to 75 mg/kg, in particular from 0.5 mg/kg to 30 mg/kg. This daily dose may be given in divided doses as necessary. Typically unit dosage forms will contain about 1 mg to 500 mg of a compound of this invention.

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition. Conventional procedures for the selection and preparation of suitable pharmaceutical formulations are described in, for example, "Pharmaceuticals—The Science of Dosage Form Designs", M. E. Aulton, Churchill Livingstone, 1988.

Thus, the present invention also provides a pharmaceutical composition comprising a compound of formula (I) or a pharmaceutically acceptable salt thereof as hereinbefore defined in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions of this invention may be administered in a standard manner for the disease or condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more diseases or conditions referred to hereinabove such as "Symbicort" (trade mark) product.

The present invention further provides a process for the preparation of a compound of formula (I) or a pharmaceutically acceptable salt thereof as defined above which, comprises:

reaction of a compound of formula (II)

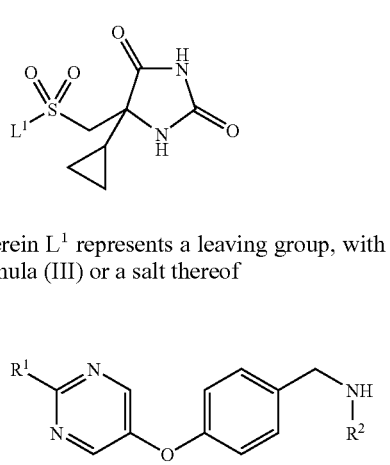

(II)

wherein $L^1$ represents a leaving group, with a compound of formula (III) or a salt thereof

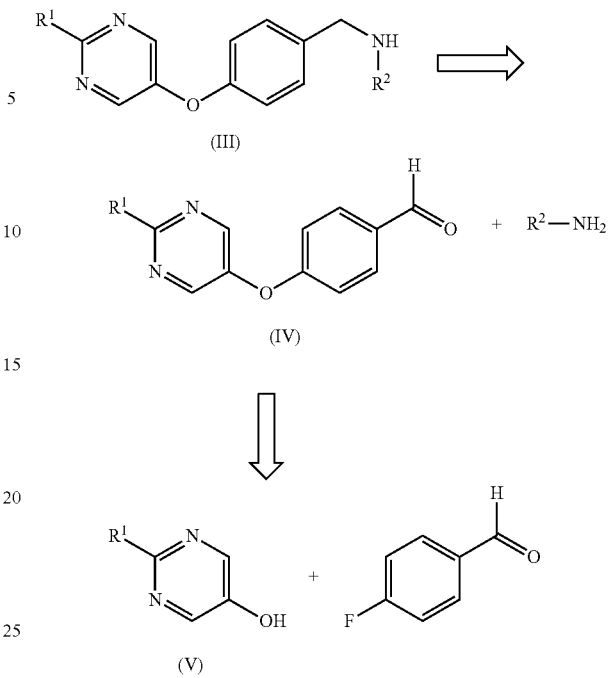

wherein $R^1$ and $R^2$ are as defined in formula (I);

and optionally thereafter forming a pharmaceutically acceptable salt thereof.

In the above process, suitable leaving groups $L^1$ include halo, particularly chloro or trifluoromethylsulfonate. The reaction is preferably performed in a suitable solvent or solvent mixture optionally in the presence of an added base for a suitable period of time, typically 0.1 to 16 h, at 0° C. to reflux temperature. Typically solvents such as N,N-dimethylformamide, pyridine, tetrahydrofuran, acetonitrile, N-methylpyrrolidine or dichloromethane are used. When used, the added base may be an organic base such as triethylamine, N,N-diisopropylethylamine (DIPEA), N-methylmorpholine or pyridine, or an inorganic base such as an alkali metal carbonate. The reaction is typically conducted at ambient temperature for 0.5 to 16 h, or until completion of the reaction has been achieved, as determined by chromatographic or spectroscopic methods. Reactions of sulfonyl halides with various primary and secondary amines are well known in the literature, and the variations of the conditions will be evident for those skilled in the art.

Sulfonylchlorides of formula (II) wherein $L^1$ represents chloro are disclosed in WO 2006/065215 and references cited therein.

Amines of formula (III) are preferably formed by reductive alkylation of the primary amine or ammonia, $R^2$—$NH_2$, with a 4-(pyrimidin-5-yloxy)-benzaldehyde of formula (IV) using standard conditions which will be readily apparent to those skilled in the art. Typically, the aldehyde (IV) is refluxed with an excess of the amine $R^2$—$NH_2$ in a solvent such as ethanol for 1 to 2 hours. The excess amine is then evaporated off and the intermediate imine is re-dissolved in ethanol. Hydrogenation at atmospheric pressure with palladium (0) on carbon for 0.5 to 2 hours at ambient temperature then affords the amine (III).

Aldehydes of formula (IV) are conveniently formed by a nucleophilic aromatic substitution reaction between 4-fluoro-benzaldehyde and the pyrimidin-5-ol (V). Reaction conditions which will be readily apparent to those skilled in the art, may involve heating with a base in a polar aprotic solvent such as tetrahydrofuran, dioxane, acetonitrile, N,N-dimethylformamide, N-methylpyrrolidine or dimethylsulfoxide. A typical procedure involves mixing 4-fluoro-benzaldehyde and a pyrimidin-5-ol (V) with excess potassium carbonate or potassium tert-butoxide in N,N-dimethylformamide or N-methylpyrrolidine and heating at 120° C. for about 16 hours to afford the aldehyde (IV).

Pyrimidin-5-ols of formula (V) can be prepared by various methods known in the art. For a comprehensive review on pyrimidine synthesis, see S. Von Angerer, Science of Synthesis, (2004), 16, 379-572. Two such routes are briefly mentioned here.

In a first route, an amidine, $R^1$—C(=NH)$NH_2$, is condensed with a N-[3-(dimethylamino)-2-hydroxyprop-2-en-1-ylidene]-N-methylmethanaminium salt, essentially as described in U.S. Pat. No. 4,558,039. The hydroxyl group is preferably protected, for example, as the benzyl ether. A suitable salt is the tetrafluoroborate.

In a second route to pyrimidin-5-ols, an alkyl ester, acid or amidine is condensed with 1,3-diamino-propan-2-ol. The resultant ring closed intermediate 1,4,5,6-tetrahydro-pyrimidin-5-ol is then oxidized to give the pyrimidin-5-ol (V). See, for example, U.S. Pat. No. 5,175,166 or Hull, J. W. J.; Otterson, K.; Rhubright, D.; J. Org. Chem. 1993, 58, 520-522. Typically, the condensation is performed in toluene or xylene at reflux temperature for 5 to 24 hours with azeotropic removal of the formed water. The tetrahydro-pyrimidine intermediate is eventually isolated as a salt, such as a hydrochloride salt. Oxidation is typically achieved using excess nitrobenzene and a base, such as sodium methoxide, potassium tert-butoxide or potassium hydroxide, at 120° C. for 1 to 5 hours. Co-solvents such as toluene or xylene may be used.

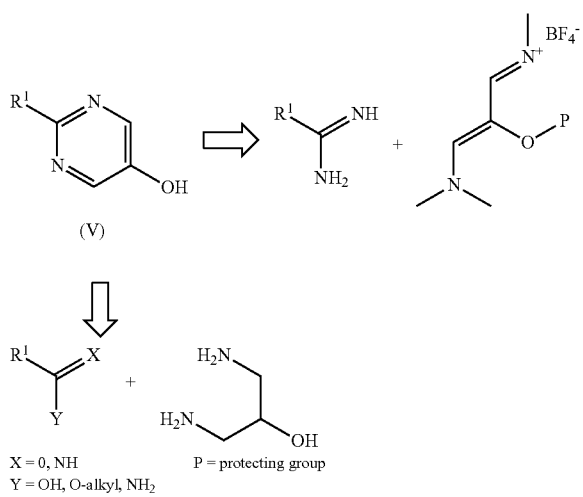

Amines of formula (III) wherein $R^2$ is H are conveniently prepared by reduction of a nitrile (VI). The nitrile (VI) may in turn be formed by a nucleophilic aromatic substitution reaction between a 4-substituted benzonitrile and a pyrimidin-5-ol by a process analogous to that described for formation of the aldehyde (IV).

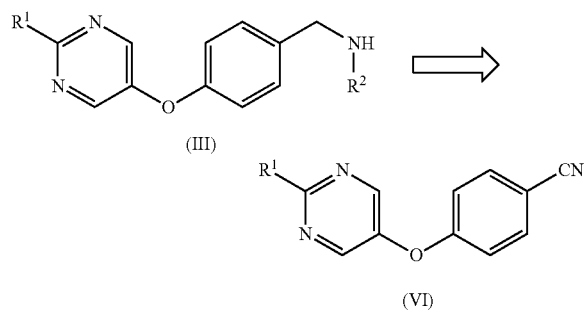

A further alternative route to amines (III) involves reduction of an amide (VII). The amide (VII) may in turn be formed by reduction of the corresponding nitrile (VI) or a synthetic equivalent thereof, followed by an N-protection, $R^2$-alkylation and deprotection procedure.

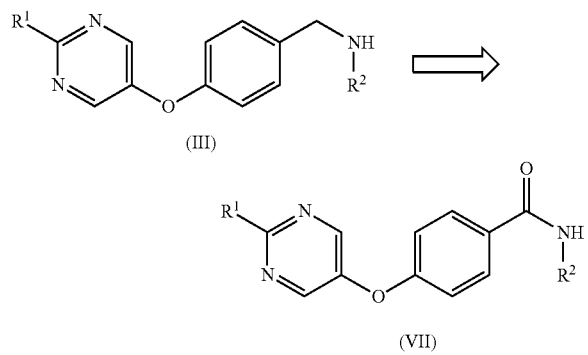

It will be appreciated by those skilled in the art that in the processes of the present invention certain potentially reactive functional groups such as hydroxyl or amino groups in the starting reagents or intermediate compounds may need to be protected by suitable protecting groups. Thus, the preparation of the compounds of the invention may involve, at various stages, the addition and removal of one or more protecting groups.

Suitable protecting groups and details of processes for adding and removing such groups are described in 'Protective Groups in Organic Chemistry', edited by J. W. F. McOmie, Plenum Press (1973) and 'Protective Groups in Organic Synthesis', 3rd edition, T. W. Greene and P. G. M. Wuts, Wiley-Interscience (1999).

Specific processes for the preparation of compounds of Formula (I) are disclosed within the Examples section of the present specification. Such processes form an aspect of the present invention.

The necessary starting materials are either commercially available, are known in the literature or may be prepared using known techniques. Specific processes for the preparation of certain key starting materials are disclosed within the Examples section of the present specification and such processes form an aspect of the present invention.

Certain novel intermediates are disclosed within the Examples section of the present specification and such intermediates form an aspect of the present invention.

Thus, in one embodiment, novel amines of formula (III) and salts thereof, wherein $R^1$ and $R^2$ are as defined above, are disclosed as intermediates useful in the preparation of compounds of formula (I).

Compounds of formula (I) can be converted into further compounds of formula (I) using standard procedures.

The compounds of the invention and intermediates thereto may be isolated from their reaction mixtures and, if necessary further purified, by using standard techniques.

The compounds of the invention may also be administered in conjunction with other compounds used for the treatment of the above conditions.

Thus, the invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, periodontal disease and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 23, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline. In addition the invention relates to a combination of a compound of the invention, or a pharmaceutically acceptable salt thereof, with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B$_1$.- or B$_2$.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK$_1$. or NK$_3$. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; or (xxvii) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In one aspect, the invention provides a pharmaceutical product comprising, in combination, two or more active ingredients including a first active ingredient which is a compound of formula (I) as defined above, and one or more further active ingredients which are selected from;
a phosphodiesterase inhibitor;
a β2-adrenoceptor agonist;
a modulator of chemokine receptor function;
an inhibitor of kinase function;
a protease inhibitor;
a glucocorticoid;
an anticholinergic agent; and
a non-steroidal glucocorticoid receptor agonist.

Examples of a phosphodiesterase inhibitor are a PDE4 inhibitor, including an inhibitor of the isoform PDE4D, or a PDE5 inhibitor; examples of a selective β2-adrenoceptor agonist include metaproterenol, isoproterenol, isoprenaline, albuterol, salbutamol, formoterol, salmeterol, terbutaline, orciprenaline, bitolterol mesylate, pirbuterol or indacaterol; examples of a muscarinic receptor antagonist are a M1, M2 or M3 antagonist, such as a selective M3 antagonist such as ipratropium bromide, tiotropium bromide, oxitropium bromide, pirenzepine or telenzepine; examples of a modulator of chemokine receptor function are a CCR1 receptor antagonist; examples of a kinase inhibitor are an inhibitor of p38 or IKK2 function; examples of a protease inhibitor are a neutrophil elastase inhibitor; examples of a glucocorticoid include flunisolide, triamcinolone acetonide, beclomethasone dipropionate, budesonide, fluticasone propionate, ciclesonide or mometasone furoate.

The present invention will now be further explained by reference to the following illustrative examples.

General Methods $^1$H NMR spectra were recorded on a Varian Inova 400 MHz or a Varian Mercury-VX 300 MHz instrument. The central peaks of chloroform-d ($\delta_H$ 7.27 ppm), dimethyl-sulfoxide-d$_6$ ($\delta_H$ 2.50 ppm) or methanol-d$_4$ ($\delta_H$ 3.31 ppm) were used as internal references. The following abbreviations have been used: s, singlet; br s, broad singlet; d, doublet; dd, double doublet; ddd, double double doublet; t, triplet; dt, double triplet; q, quartet; m, multiplet. For multiplets the chemical shift value is given either for the center of the signal or as a range. Analytical thin-layer chromatography was carried out on silica gel 60 (Merck) plates with fluorescent indicator. Column chromatography was carried out on silica gel (0.040-0.063 mm, Merck) with a slight over-pressure (0.2-0.4 bar) applied to the column. For preparative HPLC a Kromasil KR-100-5-C$_{18}$ column (250×20 mm, Akzo Nobel) and mixtures of acetonitrile and water (with 0.1 vol % trifluoroacetic acid added where indicated) at a flow rate of 10 mL per minute were used. Fractions containing the desired compound were combined, concentrated by rotary evaporation and finally freeze-dried. Unless stated otherwise starting materials were commercially available. All solvents and commercial reagents were of laboratory grade and were used as received. Operations were carried out at ambient temperature, i.e. in the range 17 to 25° C. and under an atmosphere of an inert gas such as argon unless otherwise stated. Reaction times may be shorter or longer than indicated to complete the reactions in the Examples. Organic phases from extractions were dried over anhydrous sodium sulfate if not stated otherwise and concentrated by rotary evaporation. Yields were not optimised.

The Following Method was Used for LC-MS Analysis:

Instrument Agilent 1100; Column Waters Symmetry 2.1× 30 mm; Mass APCI; Flow rate 0.7 mL/min; Wavelength 254 or 220 nm; Solvent A: water+0.1% TFA; Solvent B: acetonitrile+0.1% TFA; Gradient 15-95%/B 2.7 min, 95% B 0.3 min.

The Following Method was Used for GC-MS Analysis:

Instrument Hewlett Packard 5890 Series II; Column Agilent HP-5 (30 m×0.32 mm ID); Mass selective detector Hewlett Packard 5971 Series; Pressure 55 kPa He; Oven program 100° C. (3 min) to 300° C., 25° C./min.

Abbreviations:

| | |
|---|---|
| DIPEA | N,N-diisopropylethylamine |
| DMF | N,N-dimethylformamide |
| DMSO | dimethylsulfoxide |
| EtOAc | ethyl acetate |
| EtOH | ethanol |
| GC-MS | gas chromatography-mass spectrometry |
| HPLC | high-performance liquid chromatography |
| LC-MS | liquid chromatography-mass spectroscopy |
| MeCN | acetonitrile |
| MeOH | methanol |
| NMP | N-methylpyrrolidinone |
| Rt | retention time |
| THF | tetrahydrofuran |
| TBME | tert-butyl methyl ether |
| TFA | trifluoroacetic acid |

EXAMPLE 1

1-[(4S)-4-Cyclopropyl-2,5-dioxoimidazolidin-4-yl]-N-methyl-N-{[4-(pyrimidin-5-yloxy)phenyl]methyl}methanesulfonamide trifluoroacetic acid salt

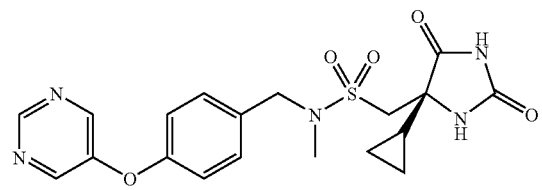

N-Methyl-N-{[4-(pyrimidin-5-yloxy)phenyl]methyl}amine (0.043 g, 0.20 mmol) was stirred in NMP (1.0 mL). The mixture was cooled using a cold water bath and DIPEA (36 µL, 0.22 mmol) was added, followed by the portionwise addition of (4S)-(4-cyclopropyl-2,5-dioxoimidazolidin-4-yl)methanesulfonyl chloride (WO 2006/065215; 0.051 g, 0.20 mmol) over 5 minutes. After 10 minutes water was added and the product extracted three times with EtOAc. The extracts were washed with brine, dried and concentrated. The product was purified by preparative HPLC (0.1% TFA in eluent) to give 0.057 g (66%) of the title compound as the trifluoroacetic acid salt.

APCI-MS m/z: 432 (M+1).

$^1$H NMR (DMSO-d$_6$): δ 0.12-0.26 (m, 1H), 0.35-0.58 (m, 3H), 1.12-1.22 (m, 1H), 2.67 (s, 3H), 3.60 (d, 2H), 4.25 (q, 2H), 7.28 (q, 4H), 7.97 (d, 1H), 8.63 (s, 2H), 9.01 (s, 1H), 10.74 (s, 1H) ppm.

The starting materials were prepared as follows:

a) 5-(Methyloxy)pyrimidine

Prepared as in *Chem. Eur. J.* 2003, 9, 4997-5010 on a 31 mmol scale with a yield of 47% after purification.

$^1$H NMR (CDCl$_3$): δ 3.93 (s, 3H), 8.42 (s, 2H), 8.86 (s, 1H) ppm.

b) Pyrimidin-5-ol

Prepared as in *Chem. Eur. J.* 2003, 9, 4997-5010 on a 15 mmol scale with a yield of 27% after purification.

$^1$H NMR (DMSO-d$_6$): δ 8.33 (s, 2H), 8.66 (s, 1H), 10.45 (s, 1H) ppm.

c) 4-(Pyrimidin-5-yloxy)benzaldehyde

To a stirred solution of pyrimidin-5-ol (0.384 g, 4.0 mmol) in DMF (4.0 mL) were added 4-fluorobenzaldehyde (0.429 g, 4.0 mmol), sodium methanesulphinate (0.118 g, 1.0 mmol) and potassium carbonate (0.828 g, 6.0 mmol). The reaction mixture was heated at 120° C. for 3 hours, cooled to ambient temperature, treated with water and extracted three times with TBME. The extracts were washed with brine, dried and concentrated. Column chromatography gave 0.523 g (43%) of the subtitle compound.

APCI-MS m/z: 201 (M+1).

$^1$H NMR (CDCl$_3$): δ 7.15 (dd, 2H), 7.93 (dt, 2H), 8.58 (s, 2H), 9.13 (s, 1H), 9.98 (s, 1H) ppm.

d) N-Methyl-N-{[4-(pyrimidin-5-yloxy)phenyl]methyl}amine 4-(Pyrimidin-5-yloxy)benzaldehyde (0.344 g, 1.7 mmol) was stirred with 33% methylamine in EtOH (30 mL) at reflux for 3 hours and then concentrated. The residue was dissolved in MeOH and treated with sodium borohydride (0.195 g, 5.2 mmol) over 1 hour and stirred for a further 1 hour. Water was added and the product was extracted three times with EtOAc. The organic phases were combined, washed with brine, dried and concentrated to give 0.267 g (100%) of product that was used without further purification.

APCI-MS m/z: 216 (M+1).

$^1$H NMR (CDCl$_3$): δ 2.38 (s, 3H), 3.68 (s, 2H), 6.94 (d, 2H), 7.28 (d, 2H), 8.38 (d, 2H), 8.87 (s, 1H) ppm.

EXAMPLE 2

1-[(4S)-4-Cyclopropyl-2,5-dioxoimidazolidin-4-yl]-N-({4-[(2-cyclopropylpyrimidin-5-yl)oxy]phenyl}methyl)-N-methylmethanesulfonamide

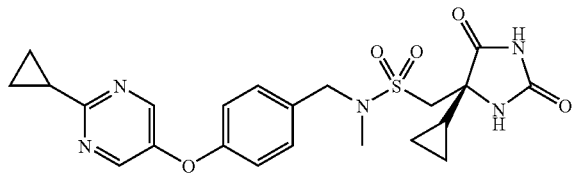

Crude {4-[(2-cyclopropylpyrimidin-5-yl)oxy]benzyl}methylamine dihydrochloride (0.115 g, 0.35 mmol) was dissolved in NMP (2.0 mL), THF (2.0 mL) and DIPEA (0.30 mL, 1.8 mmol) to form a yellow solution. (4S)-(4-Cyclopropyl-2,5-dioxoimidazolidin-4-yl)methanesulfonyl chloride (WO 2006/065215; 0.070 g, 0.28 mmol) was added portionwise during 5 minutes and the reaction mixture was stirred for 1 hour. The solvent was removed by evaporation and the residue was diluted with water and extracted twice with EtOAc. The combined organic phases were washed with water and concentrated. The crude product was purified by HPLC, using a 35 minutes gradient of 20% to 90% MeCN in water to give 0.081 g (61% yield) of the title compound as a colourless powder.

APCI-MS m/z 472.1 (M+1); Rt=1.93 min.

$^1$H-NMR (DMSO-d$_6$): δ 0.14-0.24 (m, 1H), 0.33-0.57 (m, 3H), 0.96 (m, 2H), 1.03 (m, 2H), 1.15 (m, 1H), 2.22 (m, 1H), 2.65 (s, 3H), 3.44 (d, 1H), 3.75 (d, 1H), 4.23 (q, 2H), 7.09 (d, 2H), 7.34 (d, 2H), 7.96 (s, 1H), 8.45 (s, 2H), 10.74 (s, 1H) ppm.

The starting materials were prepared as follows:

a) 5-(Benzyloxy)-2-cyclopropylpyrimidine

The subtitle compound was synthesised using the method described in U.S. Pat. No. 4,558,039, starting from cyclopropylcarbamidine hydrochloride.

LC-APCI-MS m/z 227.0 (M+1); Rt=2.36 min.

$^1$H-NMR (DMSO-d$_6$): δ 0.86-0.99 (m, 4H), 2.14 (m, 1H), 5.21 (s, 2H), 7.31-7.47 (m, 5H), 8.44 (s, 2H) ppm.

b) 2-Cyclopropylpyrimidin-5-ol 5-(Benzyloxy)-2-cyclopropylpyrimidine (4.0 g, 18 mmol) was dissolved in MeOH (100 mL) and 10% palladium on carbon (0.170 g) was added. The mixture was hydrogenated at ambient temperature and 1.013 bar pressure overnight. Filtration and concentration gave a crude product that was filtered through a short silica gel column using 5% MeOH-EtOAc as eluent. Evaporation of the solvent gave 1.3 g (54% yield) of the subtitle compound as a colourless solid.

GC-MS m/z 136.0 M$^+$ (41% relative intensity) 135.0 (100% relative intensity); Rt=7.36 min.

$^1$H-NMR (DMSO-d$_6$): δ 0.80-0.96 (m, 4H), 2.09 (m, 1H), 8.17 (s, 2H), 10.02 (s, 1H) ppm.

c) 4-[(2-Cyclopropylpyrimidin-5-yl)oxy]benzaldehyde

2-Cyclopropylpyrimidin-5-ol (0.272 g, 2.0 mmol), 4-fluorobenzaldehyde (0.22 mL, 2.1 mmol) and potassium carbonate (0.414 g, 3.0 mmol) in dry DMF (2.0 mL) were heated to 120° C. in a sealed tube for 3 hours. The slurry was diluted with water and extracted twice with EtOAc. The combined organic phases were washed three times with water and brine, dried, filtered and concentrated to give a yellow oil. Purification by column chromatography using 20 g silica and a gradient of 0% to 50% EtOAc-heptanes as eluent gave 0.478 g (99% yield) of the subtitle compound as a colourless oil.

LC-APCI-MS m/z 241.1 (M+1); Rt=1.98 min.
$^1$H-NMR (CDCl$_3$): δ 1.04-1.17 (m, 4H), 2.30 (m, 1H), 7.07 (d, 2H), 7.88 (d, 2H), 8.40 (s, 2H), 9.94 (s, 1H) ppm.

d) {4-[(2-Cyclopropylpyrimidin-5-yl)oxy]benzyl}methylamine dihydrochloride

To a solution of 4-[(2-cyclopropylpyrimidin-5-yl)oxy]benzaldehyde (0.240 g, 1.0 mmol) in MeCN (0.50 mL) was added 2M methylamine in THF (2.0 mL, 4.0 mmol) followed by sodium borohydride (0.120 g, 3.2 mmol) and MeCN (0.50 mL). The slurry was stirred for 30 minutes. The solvents were removed by evaporation, water was added and the mixture was extracted with EtOAc. The organic phase was washed with brine and evaporated onto silica gel. This gel was applied onto a 20 g silica gel column. Column chromatography using a gradient of 10% to 60% EtOAc in heptanes eluted impurities. Elution with 10% MeOH in EtOAc (100 mL) followed by 5% concentrated NH$_3$ in MeOH (100 mL) gave the product in the basic fractions. These fractions were combined, concentrated and re-dissolved in water. The pH was adjusted to 13 to 14 using sodium hydroxide solution and the mixture was extracted several times with EtOAc. The organic extracts were washed with brine, dried over potassium carbonate, filtered and concentrated to give an oily residue. This oil was dissolved in EtOAc and an excess of a 1.5M solution of hydrogen chloride in EtOAc was added. The solvent was removed by evaporation to give 0.186 g (56% yield) of the crude subtitle compound. The salt obtained was 93.9% pure and was used without further purification.

LC-APCI-MS m/z 256.1 (M+1−2 HCl); Rt=1.49 min.
$^1$H-NMR (CD$_3$OD): δ 1.21-1.44 (m, 4H), 2.36 (m, 1H), 2.74 (s, 3H), 4.22 (s, 2H), 7.26 (d, 2H), 7.60 (d, 2H), 8.72 (s, 2H) ppm.

EXAMPLE 3

1-[(4S)-4-Cyclopropyl-2,5-dioxoimidazolidin-4-yl]-N-methyl-N-({4-[(2-methylpyrimidin-5-yl)oxy]phenyl}methyl)methanesulfonamide

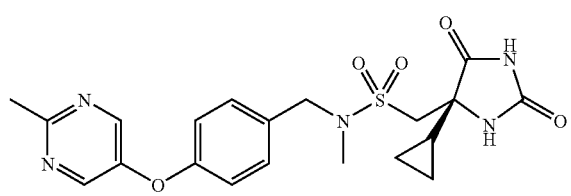

Prepared as in Example 1 but starting from N-methyl-1-{4-[(2-methylpyrimidin-5-yl)oxy]-phenyl}methanamine on a 0.50 mmol scale with a yield of 61% after purification.

APCI-MS m/z 446 (M+1).
$^1$H NMR (DMSO-d$_6$): δ 0.13-0.24 (m, 1H), 0.33-0.57 (m, 3H), 1.15 (ddd, 1H), 2.61 (d, 3H), 2.66 (s, 3H), 3.60 (dd, 2H), 4.23 (dd, 2H), 7.11 (dd, 2H), 7.35 (dd, 2H), 7.97 (s, 1H), 8.52 (s, 2H), 10.74 (s, 1H) ppm.

The starting materials were prepared as follows:

a) 2-Methyl-5-[(phenylmethyl)oxy]pyrimidine

Prepared as in Example 2(a) on a 15 mmol scale with a yield of 73% after purification.

APCI-MS m/z: 201 (M+1).
$^1$H NMR (CDCl$_3$): δ 2.67 (s, 3H), 5.13 (s, 2H), 7.31-7.50 (m, 5H), 8.37 (s, 2H) ppm.

b) 2-Methylpyrimidin-5-ol

Prepared as in Example 2(b) on an 11 mmol scale with a yield of 100% and used without further purification.
$^1$H NMR (DMSO-d$_6$): δ 8.10 (s, 2H), 2.50 (s, 3H) ppm.

c) 4-[(2-Methylpyrimidin-5-yl)oxy]benzaldehyde

Prepared as in Example 1(c) on an 11 mmol scale with a yield of 22% after purification.

APCI-MS m/z 214 (M+1).
$^1$H NMR (CDCl$_3$): δ 2.78 (s, 3H), 7.11 (dd, 2H), 7.91 (dd, 2H), 8.49 (s, 2H), 9.97 (s, 1H) ppm.

d) N-Methyl-1-{4-[(2-methylpyrimidin-5-yl)oxy]phenyl}methanamine

Prepared as in Example 1(d) on a 2.4 mmol scale with a yield of 82% after purification.

APCI-MS m/z 228 (M+1).
$^1$H NMR (CDCl$_3$): δ 2.46 (s, 3H), 2.72 (s, 3H), 3.74 (s, 2H), 6.98 (d, 2H), 7.33 (d, 2H), 8.38 (s, 2H) ppm.

EXAMPLE 4

1-[(4S)-4-Cyclopropyl-2,5-dioxoimidazolidin-4-yl]-N-methyl-N-[(4-{[2-(trifluoromethyl)pyrimidin-5-yl]oxy}phenyl)methyl]methanesulfonamide

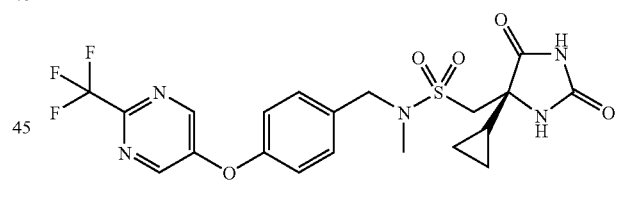

Prepared as in Example 1 but starting from N-methyl-N-[(4-{[2-(trifluoromethyl)pyrimidin-5-yl]oxy}phenyl)methyl]amine on a 0.60 mmol scale with a yield of 7.5% after purification.

APCI-MS m/z 500 (M+1).
$^1$H NMR (DMSO-d$_6$): δ 0.14-0.25 (m, 1H), 0.46 (m, 3H), 1.16 (m, 1H), 2.68 (s, 3H), 3.47 (d, 3H), 3.77 (d, 1H), 4.28 (m, 2H), 7.30 (d, 2H), 7.42 (d, 2H), 7.98 (br s, 1H), 8.81 (s, 2H), 10.75 (br s, 1H) ppm.

The starting materials were prepared as follows:

a) 2-(Trifluoromethyl)-1,4,5,6-tetrahydropyrimidin-5-ol hydrochloride

The free base was prepared as described in U.S. Pat. No. 5,175,166 on a 114 mmol scale. The crude product was dissolved in propan-2-ol, treated with 6M hydrogen chloride in propan-2-ol and the product filtered off as white crystals in a yield of 86%.

APCI-MS m/z 169 (M+1).
$^1$H NMR (DMSO-d$_6$): δ 3.39 (d, 2H), 3.51 (d, 2H), 4.25 (q, 1H), 6.32 (s, 1H), 12.11 (s, 1H) ppm.

b) 2-(Trifluoromethyl)pyrimidin-5-ol 2-(Trifluoromethyl)-1,4,5,6-tetrahydropyrimidin-5-ol (4.20 g, 25 mmol) was stirred in nitrobenzene at 90° C. Sodium methoxide (5.4 g, 100 mmol) was dissolved in methanol (75 ml) and added portionwise to the reaction mixture, allowing the methanol to distill off before the next addition. The reaction mixture was then warmed to 121° C. for one hour, cooled, shaken with water (150 ml), the organic phase separated off and the aqueous phase washed with ethyl acetate (2×100 ml). The aqueous phase was adjusted to pH 4.0 with 6M aqueous hydrochloric acid, extracted with ethyl acetate (2×100 ml), dried and evaporated to give 2.53 g (61.7%) of an orange coloured product that was used without further purification.
APCI-MS m/z 165 (M+1).
$^1$H NMR (DMSO-d$_6$): δ 8.54 (s, 2H), 11.48 (s, 1H) ppm.

c) 4-{[2-(Trifluoromethyl)pyrimidin-5-yl]oxy}benzaldehyde

Prepared as in Example 1(c) on a 5.0 mmol scale with a yield of 74%.
GC-MS m/z=268 (M$^+$).
$^1$H NMR (DMSO-d$_6$): δ 7.44 (d, 2H), 7.99 (d, 2H), 8.95 (s, 2H), 9.97 (d, 1H) ppm.

d) N-Methyl-N-[(4-{[2-(trifluoromethyl)pyrimidin-5-yl]oxy}phenyl)methyl]amine>

4-{[2-(Trifluoromethyl)pyrimidin-5-yl]oxy}benzaldehyde was stirred with 33% methylamine in 95% ethanol (30 mL) at reflux for 1 hour and then concentrated. The residue was re-dissolved in 95% ethanol, 10% palladium/carbon was added, and the mixture was hydrogenated at room temperature under atmospheric pressure for 30 minutes. The reaction was performed on a 5.0 mmol scale with a yield of 95%.
APCI-MS m/z 284 (M+1).
$^1$H NMR (CDCl$_3$): δ 2.49 (s, 3H), 3.80 (s, 2H), 5.30 (s, 1H), 7.08 (dd, 2H), 7.43 (dd, 2H), 8.53 (s, 2H) ppm.

EXAMPLE 5

1-[(4S)-4-Cyclopropyl-2,5-dioxoimidazolidin-4-yl]-N-({4-[(2-ethylpyrimidin-5-yl)oxy]phenyl}methyl)-N-methylmethanesulfonamide

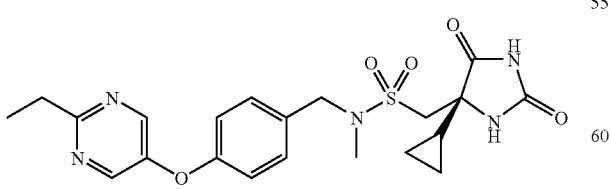

Prepared as in Example 1 but starting from [4-(2-ethylpyrimidin-5-yloxy)benzyl]methylamine on a 1.6 mmol scale with a yield of 37% after purification.
APCI-MS m/z 460 (M+1).
$^1$H NMR (DMSO-d$_6$): δ 0.12-0.28 (m, 1H), 0.35-0.58 (m, 3H), 1.08-1.20 (m, 1H), 1.28 (t, 3H), 2.66 (s, 3H), 2.90 (q, 2H), 3.44 (d, 1H), 3.75 (d, 1H), 4.23 (dd, 2H), 7.14 (d, 2H), 7.35 (d, 2H), 7.97 (s, 1H), 8.55 (s, 2H), 10.74 (s, 1H) ppm.
The starting materials were prepared as follows:

a) 2-Ethylpyrimidin-5-ol

Prepared as in Example 2(a) and 2(b) on an 11 mmol scale with an overall yield of 69%, and used without further purification.
APCI-MS m/z 125 (M+1).
$^1$H NMR (CDCl$_3$): δ 1.25 (t, 3H), 2.8 (q, 2H), 8.28 (s, 2H), 11.3 (br s, 1H) ppm.

b) 4-(2-Ethylpyrimidin-5-yloxy)benzaldehyde

Prepared as in Example 1(c) on a 2.0 mmol scale with a yield of 83% after purification.
APCI-MS m/z 229.1 (M+1).
$^1$H NMR (DMSO-d$_6$): δ 1.31 (t, 3H), 2.94 (q, 2H), 7.24 (dd, 2H), 7.96 (d, 2H), 8.70 (s, 2H), 9.96 (s, 1H) ppm.

c) [4-(2-Ethylpyrimidin-5-yloxy)-benzyl]methylamine

Prepared as in Example 1(d) on a 1.6 mmol scale with a yield of 83% after purification.
APCI-MS m/z: 244.1 (M+1).
$^1$H NMR (DMSO-d$_6$): δ 1.25 (t, 3H), 2.22 (s, 3H), 2.86 (q, 2H), 3.58 (s, 2H), 7.01 (dd, 2H), 7.31 (d, 2H), 8.48 (s, 2H) ppm.

EXAMPLE 6

1-[(4S)-4-Cyclopropyl-2,5-dioxoimidazolidin-4-yl]-N-[(4-{[2-(trifluoromethyl)pyrimidin-5-yl]oxy}benzyl)]methane sulfonamide

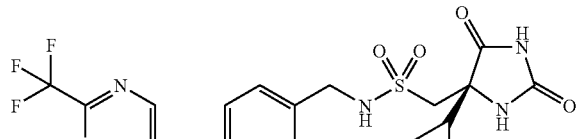

Prepared as in Example 1 but starting from (4-{[2-(trifluoromethyl)pyrimidin-5-yl]oxy}phenyl)methyl]amine on a 0.26 mmol scale with a yield of 75% after purification.
APCI-MS m/z 486.1 (M+1).
$^1$H NMR (DMSO-d$_6$): δ 0.14-0.25 (m, 1H), 0.46 (m, 3H), 1.16 (m, 1H), 3.25 (d, 1H), 3.62 (d, 1H), 4.28 (m, 2H), 7.30 (d, 2H), 7.42 (d, 2H), 7.76 (t, 1H), 7.85 (s, 1H), 8.81 (s, 2H), 10.75 (br s, 1H) ppm.
The starting materials were prepared as follows:

a) 4-{[2-(Trifluoromethyl)pyrimidin-5-yl]oxy}benzonitrile

Prepared as in Example 1(c) from 2-cyclopropylpyrimidin-5-ol and 4-fluoro-benzonitrile on a 6.1 mmol scale with a yield of 55%.
GC-MS m/z=265.1 (M$^+$).

b) 4-{[2-(Trifluoromethyl)pyrimidin-5-yl]oxy}benzylamine hydrochloride

4-{[2-(Trifluoromethyl)pyrimidin-5-yl]oxy}benzonitrile was hydrogenated in 1:1 HOAc:EtOH containing 10% Pd/C. The crude product was purified by HPLC using a 25 minutes gradient of 10% to 70% MeCN-water/TFA 0.1% to give the subtitle compound.

APCI-MS m/z 270.1 (M+1).

$^1$H NMR (DMSO-d$_6$): δ 4.8 (q, 2H), 7.35 (d, 2H), 7.56 (d, 2H), 8.18 (b, 3H), 8.79 (s, 1H) ppm.

Pharmacological Example

Isolated Enzyme Assays

MMP12

Recombinant human MMP12 catalytic domain may be expressed and purified as described by Parkar A. A. et al, (2000), Protein Expression and Purification, 20, 152. The purified enzyme can be used to monitor inhibitors of activity as follows: MMP12 (50 ng/ml final concentration) is incubated for 60 minutes at room temperature with the synthetic substrate Mca-Pro-Cha-Gly-Nva-His-Ala-Dpa-NH$_2$ (10 μM) in assay buffer (0.1M "Tris-HCl" (trade mark) buffer, pH 7.3 containing 0.1M NaCl, 20 mM CaCl$_2$, 0.020 mM ZnCl and 0.05% (w/v) "Brij 35" (trade mark) detergent) in the presence (10 concentrations) or absence of inhibitors. Activity is determined by measuring the fluorescence at λex 320 nm and λem 405 nm. Percent inhibition is calculated as follows:
% Inhibition is equal to the [Fluorescence$_{plus\ inhibitor}$−Fluorescence$_{background}$] divided by the [Fluorescence$_{minus\ inhibitor}$−Fluorescence$_{background}$].

MMP8

Purified pro-MMP8 is purchased from Calbiochem. The enzyme (at 10 μg/ml) is activated by p-amino-phenyl-mercuric acetate (APMA) at 1 mM for 2.5 h, 35° C. The activated enzyme can be used to monitor inhibitors of activity as follows: MMP8 (200 ng/ml final concentration) is incubated for 90 minutes at 35° C. (80% H$_2$O) with the synthetic substrate Mca-Pro-Cha-Gly-Nva-His-Ala-Dpa-NH$_2$ (12.5 μM) in assay buffer (0.1M "Tris-HCl" (trade mark) buffer, pH 7.5 containing 0.1M NaCl, 30 mM CaCl$_2$, 0.040 mM ZnCl and 0.05% (w/v) "Brij 35" (trade mark) detergent) in the presence (10 concentrations) or absence of inhibitors. Activity is determined by measuring the fluorescence at λex 320 nm and λem 405 nm. Percent inhibition is calculated as follows:
% Inhibition is equal to the [Fluorescence$_{plus\ inhibitor}$−Fluorescence$_{background}$] divided by the [Fluorescence$_{minus\ inhibitor}$−Fluorescence$_{background}$].

MMP9

Recombinant human MMP9 catalytic domain was expressed and then purified by Zn chelate column chromatography followed by hydroxamate affinity column chromatography. The enzyme can be used to monitor inhibitors of activity as follows: MMP9 (5 ng/ml final concentration) is incubated for 30 minutes at RT with the synthetic substrate Mca-Pro-Cha-Gly-Nva-His-Ala-Dpa-NH$_2$ (5 μM) in assay buffer (0.1M "Tris-HCl" (trade mark) buffer, pH 7.3 containing 0.1M NaCl, 20 mM CaCl$_2$, 0.020 mM ZnCl and 0.05% (w/v) "Brij 35" (trade mark) detergent) in the presence (10 concentrations) or absence of inhibitors. Activity is determined by measuring the fluorescence at λex 320 nm and λem 405 nm. Percent inhibition is calculated as follows:
% Inhibition is equal to the [Fluorescence$_{plus\ inhibitor}$−Fluorescence$_{background}$] divided by the [Fluorescence$_{minus\ inhibitor}$−Fluorescence$_{background}$].

MMP14

Recombinant human MMP14 catalytic domain may be expressed and purified as described by Parkar A. A. et al, (2000), Protein Expression and Purification, 20, 152. The purified enzyme can be used to monitor inhibitors of activity as follows: MMP14 (10 ng/ml final concentration) is incubated for 60 minutes at room temperature with the synthetic substrate Mca-Pro-Cha-Gly-Nva-His-Ala-Dpa-NH$_2$ (10 μM) in assay buffer (0.1M "Tris-HCl" (trade mark) buffer, pH 7.5 containing 0.1M NaCl, 20 mM CaCl$_2$, 0.020 mM ZnCl and 0.05% (w/v) "Brij 35" (trade mark) detergent) in the presence (5 concentrations) or absence of inhibitors. Activity is determined by measuring the fluorescence at λex 320 nm and λem 405 nm. Percent inhibition is calculated as follows:
% Inhibition is equal to the [Fluorescence$_{plus\ inhibitor}$−Fluorescence$_{background}$] divided by the [Fluorescence$_{minus\ inhibitor}$−Fluorescence$_{background}$].

A protocol for testing against other matrix metalloproteinases, including MMP9, using expressed and purified pro MMP is described, for instance, by C. Graham Knight et al., (1992) FEBS Lett., 296 (3), 263-266.

MMP19

Recombinant human MMP19 catalytic domain may be expressed and purified as described by Parkar A. A. et al, (2000), Protein Expression and Purification, 20:152. The purified enzyme can be used to monitor inhibitors of activity as follows: MMP19 (40 ng/ml final concentration) is incubated for 120 minutes at 35° C. with the synthetic substrate Mca-Pro-Leu-Ala-Nva-Dpa-Ala-Arg-NH$_2$ (5 μM) in assay buffer (0.1M "Tris-HCl" (trade mark) buffer, pH 7.3 containing 0.1M NaCl, 20 mM CaCl$_2$, 0.020 mM ZnCl and 0.05% (w/v) "Brij 35" (trade mark) detergent) in the presence (5 concentrations) or absence of inhibitors. Activity is determined by measuring the fluorescence at λex 320 nm and λem 405 nm. Percent inhibition is calculated as follows:
% Inhibition is equal to the [Fluorescence$_{plus\ inhibitor}$−Fluorescence$_{background}$] divided by the [Fluorescence$_{minus\ inhibitor}$−Fluorescence$_{background}$].

The following table shows data for a representative selection of the compounds of the present invention compared to the structurally closest compound disclosed in WO 02/074751. Selectivity for inhibition of hMMP12 over hMMPx is defined as IC$_{50}$ (MMPx) divided by IC$_{50}$ (MMP12).

TABLE

| Compound | hMMP12 IC$_{50}$ (nM) | Selectivity for inhibition of hMMP12 over: | | | |
|---|---|---|---|---|---|
| | | hMMP9 | hMMP8 | hMMP14 | hMMP19 |
| Example 1 | 19 | >525 | 320 | >525 | >525 |
| Example 2 | 4.3 | 1440 | 2120 | >2320 | >2320 |
| Example 3 | 14 | 857 | >628 | >7142 | >2800 |
| Example 4 | 8.3 | >795 | >1168 | >3560 | >2882 |
| Example 5 | 17 | 523 | 417 | >588 | >588 |

TABLE-continued

| Compound | hMMP12 IC$_{50}$ (nM) | Selectivity for inhibition of hMMP12 over: | | | |
| --- | --- | --- | --- | --- | --- |
| | | hMMP9 | hMMP8 | hMMP14 | hMMP19 |
| Example 6 | 63.7 | 1530 | 657 | — | — |
| 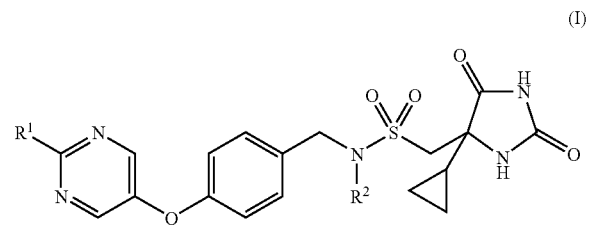 | 151 | 261 | 202 | >330 | >330 |

As can be clearly seen from the data disclosed in the Table, the compounds of the present invention are, when compared with 1-[(4S)-4-methyl-2,5-dioxoimidazolidin-4-yl]-N-[(4-phenoxy)phenyl)methyl]methanesulfonamide, on the one hand, very significantly more potent as inhibitors of hMMP12; and on the other hand, significantly more selective with respect to the inhibition of other hMMPs, particularly hMMP9.

What is claimed is:

1. A compound of formula (I) or a pharmaceutically acceptable salt thereof

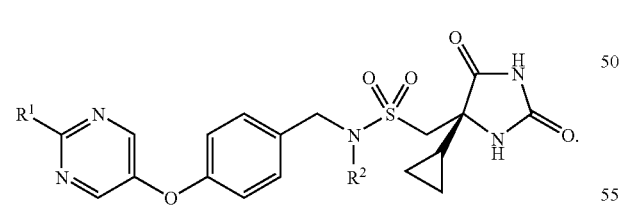

(I)

wherein
R$^1$ represents H, CH$_3$, CH$_3$CH$_2$, CF$_3$ or cyclopropyl; and
R$^2$ represents H or CH$_3$.

2. A compound according to claim 1 having the (4S)-stereochemistry as shown below:

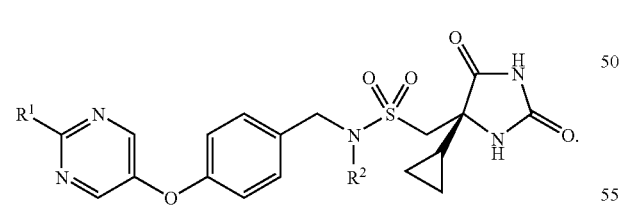

3. A compound according to claim 1 or claim 2, wherein R$^2$ represents methyl.
4. A compound according to claim 1, wherein R$^1$ represents cyclopropyl or CF$_3$.
5. A compound according to claim 1, wherein R$^1$ represents cyclopropyl.
6. A compound according to claim 1, wherein R$^1$ represents CF$_3$.
7. A compound according to claim 1 which is selected from the group consisting of:

1-[(4S)-4-cyclopropyl-2,5-dioxoimidazolidin-4-yl]-N-methyl-N-{[4-(pyrimidin-5-yloxy)phenyl]methyl}methanesulfonamide;
1-[(4S)-4-cyclopropyl-2,5-dioxoimidazolidin-4-yl]-N-({4-[(2-cyclopropylpyrimidin-5-yl)oxy]phenyl}methyl)-N-methylmethanesulfonamide;
1-[(4S)-4-cyclopropyl-2,5-dioxoimidazolidin-4-yl]-N-methyl-N-({4-[(2-methylpyrimidin-5-yl)oxy]phenyl}methyl)methanesulfonamide;
1-[(4S)-4-cyclopropyl-2,5-dioxoimidazolidin-4-yl]-N-methyl-N-[(4-{[2-(trifluoromethyl)pyrimidin-5-yl]oxy}phenyl)methyl]methanesulfonamide;
1-[(4S)-4-cyclopropyl-2,5-dioxoimidazolidin-4-yl]-N-({4-[(2-ethylpyrimidin-5-yl)oxy]phenyl}methyl)-N-methylmethanesulfonamide;
1-[(4S)-4-cyclopropyl-2,5-dioxoimidazolidin-4-yl]-N-[(4-{[2-(trifluoromethyl)pyrimidin-5-yl]oxy}benzyl)]methane sulfonamide;

and pharmaceutically acceptable salts thereof.

8. A process for the preparation of a compound of formula (I) as defined in claim 1 or a pharmaceutically acceptable salt thereof which comprises:
reaction of a compound of formula (II)

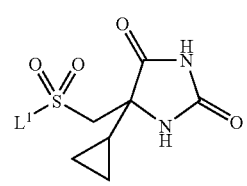

(II)

wherein L$^1$ represents a leaving group, with a compound of formula (III) (or a salt thereof)

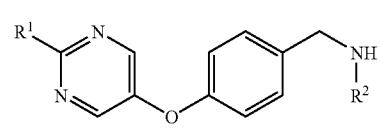

(III)

wherein R$^1$ and R$^2$ are as defined in formula (I);

and optionally thereafter forming a pharmaceutically acceptable salt thereof.

9. A compound of formula (III) or a salt thereof

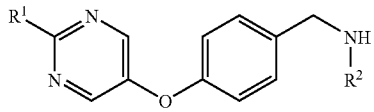

(III)

wherein:

$R^1$ represents H, $CH_3$, $CH_3CH_2$, $CF_3$ or cyclopropyl; and
$R^2$ represents H or $CH_3$.

10. A pharmaceutical composition comprising a compound of formula (I) or a pharmaceutically acceptable salt thereof as claimed in claim 1 in association with a pharmaceutically acceptable adjuvant, diluent or carrier.

11. A process for the preparation of a pharmaceutical composition which comprises mixing a compound of formula (I) or a pharmaceutically acceptable salt thereof as defined in claim 1 with a pharmaceutically acceptable adjuvant, diluent or carrier.

* * * * *